(12) United States Patent
Barry et al.

(10) Patent No.: US 8,147,532 B2
(45) Date of Patent: Apr. 3, 2012

(54) DETERMINING PATIENT-SPECIFIC VAPOR TREATMENT AND DELIVERY PARAMETERS

(75) Inventors: Robert L. Barry, Kirkland, WA (US); Brian Cran, Seattle, WA (US); Erik Henne, Seattle, WA (US); Daniel Reddy, Seattle, WA (US); Dean Corcoran, Bothell, WA (US)

(73) Assignee: Uptake Medical Corp., Seattle, WA (US)

( * ) Notice: Subject to any disclaimer, the term of this patent is extended or adjusted under 35 U.S.C. 154(b) by 684 days.

(21) Appl. No.: 12/256,197

(22) Filed: Oct. 22, 2008

(65) Prior Publication Data

US 2009/0138001 A1 May 28, 2009

Related U.S. Application Data

(60) Provisional application No. 60/981,701, filed on Oct. 22, 2007.

(51) Int. Cl.
*A61H 33/00* (2006.01)
(52) U.S. Cl. ............................ 607/83; 222/3
(58) Field of Classification Search .................. 34/271, 34/274, 293, 298; 222/3; 606/27, 83
See application file for complete search history.

(56) References Cited

U.S. PATENT DOCUMENTS

| | | |
|---|---|---|
| 3,880,168 A | 4/1975 | Berman |
| 4,773,410 A | 9/1988 | Blackmer et al. |
| 4,793,352 A | 12/1988 | Eichenlaub |
| 4,915,113 A | 4/1990 | Holman |
| 4,950,266 A | 8/1990 | Sinofsky |
| 5,006,119 A | 4/1991 | Acker et al. |
| 5,011,566 A | 4/1991 | Hoffman |
| 5,084,043 A | 1/1992 | Hertzmann et al. |
| 5,112,328 A | 5/1992 | Taboada et al. |
| 5,158,536 A | 10/1992 | Sekins et al. |
| 5,263,951 A | 11/1993 | Spears et al. |
| 5,331,947 A | 7/1994 | Shturman |
| 5,334,190 A | 8/1994 | Seiler |
| 5,348,551 A | 9/1994 | Spears et al. |
| 5,352,512 A | 10/1994 | Hoffman |
| 5,424,620 A | 6/1995 | Cheon et al. |

(Continued)

FOREIGN PATENT DOCUMENTS

WO WO 00/11927 A2 3/2000

(Continued)

OTHER PUBLICATIONS

Coda, et al., "Effects of pulmonary reventilation on gas exchange after cryolytic disobstruction of endobronchial tumors," Minerva Medical, vol. 72, pp. 1627-1631, Jun. 1981 (w/ Eng. Trans.).

(Continued)

*Primary Examiner* — Jackie Ho
*Assistant Examiner* — Gerald Landry, II
(74) *Attorney, Agent, or Firm* — Shay Glenn LLP (57) ABSTRACT

Methods and systems for determining patient specific treatment parameters for delivering vapor to the lung to treat lung tissue. In some embodiments vapor is delivered to the lung to cause coagulative necrosis, inducing fibrosis and thereby reducing the volume of at least one segment of the lung. The delivery parameters can be adjusted depending on the desired degree of injury to be induced in the lung tissue.

17 Claims, 5 Drawing Sheets

U.S. PATENT DOCUMENTS

| | | | |
|---|---|---|---|
| 5,462,521 A | 10/1995 | Brucker et al. | |
| 5,500,012 A | 3/1996 | Brucker et al. | |
| 5,503,638 A | 4/1996 | Cooper et al. | |
| 5,524,620 A | 6/1996 | Rosenschein | |
| 5,529,076 A | 6/1996 | Schachar | |
| 5,549,628 A | 8/1996 | Cooper et al. | |
| 5,562,608 A * | 10/1996 | Sekins et al. | 604/20 |
| 5,575,803 A | 11/1996 | Cooper et al. | |
| 5,591,157 A | 1/1997 | Hennings et al. | |
| 5,620,440 A | 4/1997 | Heckele et al. | |
| 5,695,507 A | 12/1997 | Auth et al. | |
| 5,735,811 A | 4/1998 | Brisken | |
| 5,752,965 A | 5/1998 | Francis et al. | |
| 5,755,753 A | 5/1998 | Knowlton | |
| 5,782,914 A | 7/1998 | Schankereli | |
| 5,800,482 A | 9/1998 | Pomeranz et al. | |
| 5,824,703 A | 10/1998 | Clark, Jr. | |
| 5,827,268 A | 10/1998 | Laufer | |
| 5,913,856 A | 6/1999 | Chia et al. | |
| 5,957,919 A | 9/1999 | Laufer | |
| 5,964,752 A | 10/1999 | Stone | |
| 5,986,662 A | 11/1999 | Argiro et al. | |
| 5,989,445 A | 11/1999 | Wise et al. | |
| 6,032,077 A | 2/2000 | Pomeranz | |
| 6,053,909 A | 4/2000 | Shadduck | |
| 6,059,011 A | 5/2000 | Giolo | |
| 6,083,255 A | 7/2000 | Laufer et al. | |
| 6,099,251 A | 8/2000 | LaFleur | |
| 6,102,037 A | 8/2000 | Koch | |
| 6,113,722 A | 9/2000 | Hoffman et al. | |
| 6,130,671 A | 10/2000 | Argiro | |
| 6,139,571 A | 10/2000 | Fuller et al. | |
| 6,162,232 A | 12/2000 | Shadduck | |
| 6,194,066 B1 | 2/2001 | Hoffman | |
| 6,200,333 B1 | 3/2001 | Laufer | |
| 6,210,404 B1 | 4/2001 | Shadduck | |
| 6,219,059 B1 | 4/2001 | Argiro | |
| 6,283,989 B1 | 9/2001 | Laufer et al. | |
| 6,299,633 B1 | 10/2001 | Laufer | |
| 6,300,150 B1 | 10/2001 | Venkatasubramanian | |
| 6,312,474 B1 | 11/2001 | Francis et al. | |
| 6,327,505 B1 | 12/2001 | Medhkour et al. | |
| 6,394,949 B1 | 5/2002 | Crowley et al. | |
| 6,398,775 B1 | 6/2002 | Perkins et al. | |
| 6,409,723 B1 | 6/2002 | Edwards | |
| 6,458,231 B1 | 10/2002 | Wapner et al. | |
| 6,468,313 B1 | 10/2002 | Claeson et al. | |
| 6,488,673 B1 | 12/2002 | Laufer et al. | |
| 6,493,589 B1 | 12/2002 | Medhkour et al. | |
| 6,508,816 B2 | 1/2003 | Shadduck | |
| 6,527,761 B1 | 3/2003 | Soltesz et al. | |
| 6,585,639 B1 | 7/2003 | Kotmel et al. | |
| 6,588,613 B1 | 7/2003 | Pechenik et al. | |
| 6,592,594 B2 | 7/2003 | Rimbaugh et al. | |
| 6,599,311 B1 | 7/2003 | Biggs et al. | |
| 6,610,043 B1 | 8/2003 | Ingenito | |
| 6,652,594 B2 | 11/2003 | Francis et al. | |
| 6,653,525 B2 | 11/2003 | Ingenito et al. | |
| 6,669,694 B2 | 12/2003 | Shadduck | |
| 6,679,264 B1 | 1/2004 | Deem et al. | |
| 6,682,520 B2 | 1/2004 | Ingenito | |
| 6,692,494 B1 | 2/2004 | Cooper et al. | |
| 6,712,812 B2 | 3/2004 | Roschak et al. | |
| 6,719,738 B2 | 4/2004 | Mehier | |
| 6,755,794 B2 | 6/2004 | Soukup | |
| 6,770,070 B1 | 8/2004 | Balbierz | |
| 6,776,765 B2 | 8/2004 | Soukup et al. | |
| 6,860,847 B2 | 3/2005 | Alferness et al. | |
| 6,901,927 B2 | 6/2005 | Deem et al. | |
| 6,904,909 B2 | 6/2005 | Andreas et al. | |
| 6,907,881 B2 | 6/2005 | Suki et al. | |
| 6,911,028 B2 | 6/2005 | Shadduck | |
| 6,929,640 B1 | 8/2005 | Underwood et al. | |
| 6,986,769 B2 | 1/2006 | Nelson et al. | |
| 7,022,088 B2 | 4/2006 | Keast et al. | |
| 7,031,504 B1 | 4/2006 | Argiro et al. | |
| 7,083,612 B2 | 8/2006 | Littrup et al. | |
| 7,128,748 B2 | 10/2006 | Mooradian et al. | |
| 7,136,064 B2 | 11/2006 | Zuiderveld | |
| 7,144,402 B2 | 12/2006 | Kuester, III | |
| 7,144,588 B2 | 12/2006 | Oray et al. | |
| 7,192,400 B2 | 3/2007 | Campbell et al. | |
| 7,233,820 B2 | 6/2007 | Gilboa | |
| 7,235,070 B2 | 6/2007 | Vanney | |
| 7,335,195 B2 | 2/2008 | Mehier | |
| 7,347,859 B2 | 3/2008 | Garabedian et al. | |
| 7,517,320 B2 | 4/2009 | Wibowo et al. | |
| 7,819,908 B2 | 10/2010 | Ingenito | |
| 7,993,323 B2 * | 8/2011 | Barry et al. | 604/500 |
| 2002/0077516 A1 | 6/2002 | Flanigan | |
| 2002/0111386 A1 | 8/2002 | Sekins et al. | |
| 2002/0177846 A1 | 11/2002 | Mulier et al. | |
| 2003/0099279 A1 | 5/2003 | Venkatasubramanian et al. | |
| 2003/0181922 A1 | 9/2003 | Alferness | |
| 2004/0031494 A1 | 2/2004 | Danek et al. | |
| 2004/0038868 A1 * | 2/2004 | Ingenito | 514/4 |
| 2004/0047855 A1 | 3/2004 | Ingenito | |
| 2004/0055606 A1 | 3/2004 | Hendricksen et al. | |
| 2004/0068306 A1 * | 4/2004 | Shadduck | 607/96 |
| 2004/0199226 A1 | 10/2004 | Shadduck | |
| 2004/0244803 A1 | 12/2004 | Tanaka | |
| 2005/0016530 A1 | 1/2005 | McCutcheon et al. | |
| 2005/0166925 A1 | 8/2005 | Wilson et al. | |
| 2005/0171396 A1 | 8/2005 | Pankratov et al. | |
| 2005/0171582 A1 | 8/2005 | Matlock | |
| 2005/0203483 A1 | 9/2005 | Perkins et al. | |
| 2005/0215991 A1 | 9/2005 | Altman et al. | |
| 2005/0222485 A1 | 10/2005 | Shaw et al. | |
| 2006/0004400 A1 | 1/2006 | McGurk et al. | |
| 2006/0047291 A1 | 3/2006 | Barry | |
| 2006/0100619 A1 | 5/2006 | McClurken et al. | |
| 2006/0130830 A1 | 6/2006 | Barry | |
| 2006/0135955 A1 | 6/2006 | Shadduck | |
| 2006/0161233 A1 * | 7/2006 | Barry et al. | 607/113 |
| 2006/0162731 A1 | 7/2006 | Wondka et al. | |
| 2006/0200076 A1 | 9/2006 | Gonzalez et al. | |
| 2006/0224154 A1 | 10/2006 | Shadduck et al. | |
| 2007/0032785 A1 | 2/2007 | Diederich et al. | |
| 2007/0036417 A1 | 2/2007 | Argiro et al. | |
| 2007/0068530 A1 | 3/2007 | Pacey | |
| 2007/0091087 A1 | 4/2007 | Zuiderveld | |
| 2007/0092864 A1 | 4/2007 | Reinhardt et al. | |
| 2007/0109299 A1 | 5/2007 | Peterson | |
| 2007/0137646 A1 | 6/2007 | Weinstein et al. | |
| 2008/0033493 A1 | 2/2008 | Deckman et al. | |
| 2008/0110457 A1 | 5/2008 | Barry et al. | |
| 2008/0114297 A1 | 5/2008 | Barry et al. | |
| 2008/0132826 A1 * | 6/2008 | Shadduck et al. | 604/24 |
| 2009/0149846 A1 | 6/2009 | Hoey et al. | |
| 2009/0216220 A1 | 8/2009 | Hoey et al. | |
| 2009/0312753 A1 | 12/2009 | Shadduck et al. | |
| 2010/0204688 A1 | 8/2010 | Hoey et al. | |
| 2011/0172654 A1 | 7/2011 | Barry et al. | |

FOREIGN PATENT DOCUMENTS

| | | | |
|---|---|---|---|
| WO | WO 02/069821 A1 | 9/2002 | |
| WO | WO 03/070302 A1 | 8/2003 | |
| WO | WO 03/086498 A2 | 10/2003 | |
| WO | WO 2005/025635 A2 | 3/2005 | |
| WO | WO 2005/102175 A2 | 11/2005 | |
| WO | WO 2006/003665 A2 | 1/2006 | |
| WO | WO 2006/055695 A1 | 5/2006 | |
| WO | WO 2006/080015 A2 | 8/2006 | |
| WO | WO 2009/009398 A1 | 1/2009 | |

OTHER PUBLICATIONS

Fishman et al., A randomized trial comparing lung-volume-reduction surgery with medical therapy for severe emphysema, N Engl J Med, vol. 348, No. 21, pp. 2059-2073, May 22, 2003.

Homasson, et al., "Bronchoscopic cryotherapy for airway strictures caused by tumors," Chest, vol. 90, No. 2, pp. 159-164, Aug. 1986.

Kang, Li, "Efficient optimal net surface detection for image segmentation—from theory to practice," M.Sc. Thesis, The University of Iowa, 2003.

Marasso, et al., "Cryosurgery in bronchoscopic treatment of tracheobronchial stenosis," Chest, vol. 103, No. 2, pp. 472-474, Feb. 1993.

Marasso, et al., "Radiofrequency resection of bronchial tumours in combination with cryotherapy: evaluation of a new technique," Thorax, vol. 53, pp. 106-109, 1998.

Mathur et al., Fiberoptic bronchoscopic cryotherapy in the management of tracheobronchial obstruction, Chest, vol. 110, No. 3, pp. 718-723, Sep. 1996.

Morice et al.; Endobrinchial argon plasma coagulation for treatment of hemotysis and neoplastic airway obstruction, Chest, vol. 119, No. 3, pp. 781-787, Mar. 2001.

Moulding et al.; Preliminary studies for achieving transcervical oviduct occlusion by hot water or low-pressure steam; Advances in Planned Parenthood; vol. 12, No. 2; pp. 79-85; 1977.

Pracht, Adam, "VIDA takes new approach," Iowa City Press-Citizen, Sep. 12, 2005.

Quin, Jacquelyn, "Use of neodymium yttrium aluminum garnet laser in long-term palliation of airway obstruction," Connecticut Medicine, vol. 59, No. 7, pp. 407-412, Jul. 1995.

Sutedja, et al., "Bronchoscopic treatment of lung tumors," Elsevier, Lung Cancer, 11, pp. 1-17, 1994.

Tschirren, Juerg, "Segmentation, anatomical labeling, branchpoint matching, and quantitative analysis of human airway trees in volumetric CT images," Ph.D. Thesis, The University of Iowa, 2003.

Tschirren, Juerg, "Segmentation, anatomical labeling, branchpoint matching, and quantitative analysis of human airway trees in volumetric CT images," Slides from Ph.D. defense, The University of Iowa, 2003.

Tschirren et al.; "Intrathoracic airway trees: segmentation and airway morphology analysis from low-dose CT scans;" IEEE Trans. Med. Imaging; vol. 24, No. 12; pp. 1529-1539 (2002).

Becker, et al.; Lung volumes before and after lung volume reduction surgery; Am J Respir Crit Care Med; vol. 157; pp. 1593-1599; (1998) Oct. 28, 1997.

Blacker, G. F.; Vaporization of the uterus; J. of Obstetrics and Gynaecology; vol. 33; pp. 488-511; 1902.

Carpenter III et al.; Comparison of endoscopic cryosurgery and electrocoagulation of bronchi; Trans. Amer. Acad. Opth.; vol. 84; No. 1; pp. ORL-313-ORL-323; Jan. 1977.

Eyal et al.; The acute effect of pulmonary burns on lung mechanics and gas exchange in the rabbit; Br. J. Anaesth.; vol. 47; pp. 546-552; 1975.

Goldberg et al.; Radiofrequency tissue ablation in the rabbit lung: Efficacy and complications; Acad. Radiol.; vol. 2; pp. 776-784; 1995.

Looga, R. U.; Mechanism of changes in the respiratory and cardiovascular reflexes from the lungs associated with intrapulmonary steam burns; Eng. Trans. from Byulleten Eksperimental noi Biologii I Meditsiny; vol. 61; No. 6; pp. 31-33; Jun. 1966.

Moritz et al.; The effects of inhaled heat on the air pasage and lungs; American Journal of Pathology; vol. XXI; pp. 311-331; 1944.

Van De Velde; Vapo-cauterization of the uterus; Amer. J. Med. Sci.; vol. CXVIII; 1899.

Vorre et al.; Morphology of tracheal scar after resection with CO2-laser and high-frequency cutting loop; Acta Otolaryngol (Stockh); vol. 107; pp. 307-312; 1989.

Barry et al.; U.S. Appl. No. 12/409,370 entitled "Determining patient-specific vapor treatment and delivery parameters," filed Mar. 23, 2009.

* cited by examiner

DETERMINING PATIENT-SPECIFIC VAPOR TREATMENT AND DELIVERY PARAMETERS

CROSS-REFERENCE TO RELATED APPLICATIONS

This application claims the benefit under 35 U.S.C. §119 of U.S. Application No. 60/981,701, filed Oct. 22, 2007, the disclosure of which is incorporated herein by reference.

This application is related to the following copending patent applications: U.S. patent application Ser. No. 11/598,362, filed Nov. 13, 2006, and application Ser. No. 11/598,383, filed Nov. 13, 2006, both of which are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

Chronic Obstructive Pulmonary Disease ("COPD") is a chronic disease of the lungs, in which the fine inner structure of the lungs is destroyed over time, creating large voids within the lung, leading to trapping of inhaled air and loss of lung elasticity (hyperinflation). Common symptoms of COPD (which includes chronic bronchitis and emphysema) are shortness of breath, excessive production of sputum, and chronic cough. Persons suffering from COPD may also experience frequent and sudden worsening of symptoms (exacerbations).

COPD is characterized by pathological changes in the lungs and airways, as prolonged irritation leads to chronic inflammation that often persists even after the source of irritation (e.g., tobacco smoke) is no longer present. COPD is progressive and ultimately life-threatening disorder. Treatment can slow its progression; there is currently no cure.

Most risk factors for COPD are environmental. The most common cause of COPD is exposure to tobacco smoke, including second-hand (passive) smoking. Exposure to indoor and outdoor air pollution, or occupational exposure to dust, particulates, or toxic vapors or fumes can also cause COPD. Frequent lower respiratory tract infections during childhood can also increase susceptibility to COPD.

Current guidelines for the treatment of chronic obstructive pulmonary disease (COPD), including emphysema, call for immediate reduction of patient exposure to risk factors. Risk factors include tobacco smoking and occupational or environmental exposure to particulates or harmful gases. Smoking cessation may be accomplished through patient education and counseling; pharmacotherapeutic intervention may also be effective.

As COPD progresses, medical therapy may be initiated. The standard of care for treatment of stable Stage II (Moderate) and Stage III (Severe) COPD consists of treatment with one or more bronchodilators, including $\beta_2$ agonists, anticholinergic drugs, and methylxanthines administered orally or inhaled via nebulizer. However, there is no evidence that bronchodilators are capable of significantly improving $FEV_1$ or arresting or slowing the inexorable decline in lung function in emphysematous patients. Thus, medical therapy for COPD is primarily used for symptomatic relief, to prevent complications, to increase exercise tolerance, and to treat exacerbations of COPD.

Treatment with inhaled glucocorticosteroids, alone or in combination with bronchodilator therapy, can reduce the frequency of exacerbations and may be indicated in patients with Severe or Very Severe COPD, but is not recommended for patients with mild or moderate COPD as long-term treatment with glucocorticosteroids is associated with steroid myopathy.

Pulmonary rehabilitation, consisting of exercise training programs, nutrition counseling, and patient education are used to treat symptoms of COPD and to improve the patient's overall quality of life, particularly among patients with Stage II (Moderate), Stage III (Severe) and Stage IV (Very Severe) COPD.

Long-term (>15 hours/day) therapy with oxygen ($O_2$) increases survival in patients with COPD and has been shown to improve hemodynamics, exercise tolerance, lung mechanics, and can ameliorate mental deficits incurred through COPD-induced hypoxemia. Patients with COPD receive benefit from long-term oxygen therapy primarily through increased oxygen saturation.

Lung volume reduction surgery (LVRS), in which tissue from one or both lungs is resected in order to treat the physiological consequences of emphysema (enlargement of air spaces, destruction of diffusive capacity, decrease in elastic recoil with consequent reduction in expiratory airflow, hyperinflation, and trapping of air), was first conducted in human subjects in 1957 by Brantigan and Mueller. However, despite patient-reported symptomatic improvement, a high operative mortality rate (18%) precluded its acceptance as a treatment for COPD.

More recently, a series of clinical studies in patients with COPD, including prospective randomized trials, showed that LVRS resulted in benefit for lung function, gas exchange, and quality of life (QOL) measures. The National Emphysema Treatment Trial (NETT) randomly assigned 1218 subjects with severe emphysema to receive pulmonary rehabilitation with or without LVRS. Study results showed statistically significant improvement in exercise capacity among patients receiving both medical therapy and LVRS (15% vs. 3%; P<0.001) and a prespecified subgroup analysis showed a survival advantage at 24 months for patients with predominately upper-lobe emphysema and low baseline exercise capacity who were considered to be at high risk for death from surgery. However, subgroup analysis also suggested that high-risk patients with upper-lobe disease and high initial exercise capacity were poor candidates for LVRS due to increased mortality and lack of significant benefit.

Long-term follow-up of NETT subjects showed a survival benefit for patients assigned to LVRS plus medical therapy overall, as well as lasting improvement in exercise capacity and health-related QOL relative to the medical-therapy-only group. The subgroup of high-risk/high exercise capacity subjects receiving LVRS showed no survival benefit but demonstrated improved exercise capacity.

On the basis of these results, LVRS has been recommended as a palliative treatment for emphysema for the aforementioned sub-groups of patients. LVRS for the treatment of emphysema is also a costly procedure relative to standard medical therapy, and until more data are available, the cost-effectiveness of the procedure remains unclear.

Pharmacological approaches to treating emphysema patients have not yielded significant improvements in large randomized studies. Although LVRS has efficacy benefits, the high mortality and morbidity rates results in high costs.

Therefore, minimally invasive approaches (such as bronchoscopic LVR) that decrease mortality and morbidity while offering significant efficacy are desired.

Several bronchoscopic LVR approaches (including plugs, valves and stents) are currently under investigation. Most bronchoscopic approaches involve the blocking or occluding of major airways that supply emphysematous regions of the lung. Bronchoscopic LVR achieved through implantation of one-way endobronchial valves has been explored in human subjects in single-center pilot studies and in larger multi-center studies. In this procedure, one-way endobronchial valves are delivered bronchoscopically to the airway of the emphysematous lung region(s). The goal of the valve is to create collapse or atelectasis of the region of the lung similar to that achieved by LVRS. Initial multicenter experience with endobronchial valves suggests that the therapy is well tolerated, with a 90-day mortality of 1.02%, compared to 7.9% reported for the NETT LVRS study. A total of 53 patients out of 98 (54%) did not demonstrate clinically significant improvement in $FEV_1$ at 90 days, and only 23% showed improvement in exercise tolerance. This lack of improvement is likely attributable to collateral ventilation, which precludes lobar collapse despite occlusion of the major airways.

A bronchoscopic approach that creates consistent LVR despite the presence of collateral ventilation is desired. An approach is also desired that can be tailored, if need be, to safely and effectively treat any patient.

In addition to treating LVR, an approach is also desired that can treat a variety of other lung conditions, such as lung tumors, nodules, infiltrates, bacteria, fungi, viruses and other diseases and conditions.

SUMMARY OF THE INVENTION

The present invention relates generally to using vapor to treat lung tissue. This therapy may be called Bronchoscopic Thermal Vapor Ablation or BTVA.

One aspect of the invention provides a method of applying energy to a patient's lung tissue to reduce the volume of the lung, including the following steps: identifying at least one region of lung including the lung tissue to be treated (such as, e.g., a lung segment or sub-segment); inserting a delivery device into the lung region; and delivering vapor through the delivery device to the lung tissue to be treated at a dose between about 5 calories/gram to about 40 calories/gram, wherein the vapor undergoes a phase change to liquid, and energy released during the phase change is transferred to the lung tissue to injure the tissue. Some embodiments includes the step of heating the vapor to at least 100° C. before delivering the vapor in, e.g., a vapor generator disposed outside the patient.

The effects of the delivered vapor dose may vary. In some embodiments, the dose delivered causes the lung volume to be reduced over a period of about 4 to about 8 weeks. In some embodiments, the dose delivered causes the lung volume to be immediately reduced from shrinking and or denaturing of collagen. The energy transferred to the tissue may also cause coagulative necrosis of the lung tissue, possibly followed by fibrosis to effectively reduce the volume of the lung region. In some embodiments, the energy transferred to the tissue causes substantially no thermal fixation. In some embodiments, the delivering step includes the step of ablating microvasculature in the lung tissue.

In some embodiments, the step of delivering the vapor includes the step of delivering the vapor at a flow rate of between about 20 calories/second to about 200 calories/second. The vapor may be delivered for a duration of between about 2 seconds to about 30 seconds, or possibly for a duration between about 4 and about 10 seconds, in some embodiments. The delivered dose may be, e.g., between about 5 cal/g and about 20 cal/g, between about 5 cal/g and about 10 cal/g., or between about 20 cal/g and about 40 cal/g.

Another aspect of the invention provides a method of determining treatment parameters for applying energy to lung tissue with vapor to selectively injure the tissue, the method including the following steps: imaging at least one region of the lung including the lung tissue to be treated; determining a parameter (such as, e.g., mass and/or volume) of the lung tissue of the region to be treated based on the imaging; determining a safe and efficacious dosage for treating the tissue to cause a specific degree of injury to the lung tissue; determining an amount of energy to be delivered to the region based on the parameter of the lung tissue and the dose; and determining a duration for delivering the vapor based on the amount of energy to be delivered and an energy flow rate of a vapor delivery system. In some embodiments, the specific degree of injury to the lung tissue comprises coagulative necrosis which, in some embodiments, may cause fibrosis of the lung tissue to effectively reduces the volume of the lung.

Some embodiments of the invention also include the step of delivering the vapor to the segment of the lung at the delivery rate and for the determined duration. The vapor may be heated to at least 100° C. before delivering the vapor. In some embodiments, delivering the vapor causes the vapor to change to liquid, and the energy released during the phase change is transferred to the lung tissue of the segment or sub-segment.

In some embodiments, the step of imaging the at least one region of the lung to be treated includes the step of taking a CT scan of the at least one segment or sub-segment of the lung. The at least one segment or sub-segment of the lung to be treated may be at least one of RB1, RB2, RB3, LB1, LB2, and LB3.

In some embodiments, the step of determining an amount of energy to be delivered includes the step of multiplying the mass of the segment or sub-segment and the dosage. In some embodiments, the duration for delivering the vapor is determined by dividing the amount of energy to be delivered by the energy delivery rate of the delivery system. In some embodiments, for example, the safe and efficacious dosage for treating the tissue is between about 5 cal/g and about 40 cal/g., and the energy flow rate of the delivery system is between about 20 calories/second and about 200 calories/second.

Yet another aspect of the invention provides a method of determining treatment parameters for applying energy to lung tissue with vapor to reduce the volume of the lung, including the following steps: imaging at least one segment or sub-segment of the lung to be treated; determining a parameter (such as mass and/or volume) of the lung tissue of the segment or sub-segment to be treated based on the imaging; determining a safe and efficacious dosage for treating the tissue to cause reduction in the lung volume; determining an amount of energy to be delivered to the segment or sub-segment based on the parameter of the lung tissue and the dose; and determining a duration for delivering the vapor based on the amount of energy to be delivered and an energy flow rate of a vapor delivery system.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

The present invention relates generally to using vapor to treat lung tissue. This therapy may be called Bronchoscopic Thermal Vapor Ablation or BTVA. In general, the transfer of energy to a emphysematous lung region may result in ablation of micro vascularization which would reduce the amount of blood flowing to that region. This reduction in blood flow, along with the reduction in ventilation to poorly functioning regions of lung, could result in more blood flow to better functioning regions of lung. This could result in an increase in diffusion capacity (DLCO). Increases in DLCO could result in several potential benefits to the patient including increase in exercise capacity, reduction in dyspnea (shortness of breath) and reduction in the need for supplemental oxygen.

The application of vapor could invoke lung growth which could result in an increase in pulmonary flow and or parenchyma volume or mass that might result in increased diffusion capacity (DLCO) without measurable changes in Residual Volume (RV), FEV1, FRC or other mechanical pulmonary function measures. Increases in DLCO could result in several potential benefits to the patient including increase in exercise capacity, reduction in dyspnea, and reduction in the need for supplemental oxygen. The reduction in blood flow and ventilation by virtue of LVR may also result in an increase in the matching of perfusion and ventilation (VQ match).

More specifically, the invention relates to determining delivery parameters (e.g., vapor dose, flow rate of a delivery system) for delivering vapor to the lung to induce a desired degree of injury to the tissue. The energy transferred to the tissue causes injury and subsequent lung growth signals that stimulate new lung tissue in either the treated region of lung or throughout the entire lung. Treatment of the lung as used herein refers to substantially immediate effects on the lung tissue as well as effects over a longer period time, and can be on the order of weeks, months, or even years. The delivery parameters can depend on the amount (e.g., mass or volume) of lung to be treated as well as the desired degree of injury to the tissue (e.g., coagulative necrosis, thermal fixation).

While delivering vapor to the lung to cause tissue fibrosis to reduce the volume of the lung is one use of vapor treatment, it is understood that the invention includes administering vapor to the lung to treat a variety of conditions and diseases. For example, vapor can be used in the treatment of tumors, lung cancer, solitary pulmonary nodule, lung abscesses, tuberculosis, and other lung diseases. The condition to be treated, and specifically the desired degree of injury (immediate and/or longer term) to the lung tissue, can partially determine the treatment and delivery parameters.

One type of injury that may be a desired result of the vapor treatment is coagulative necrosis or fibrosis. Coagulative necrosis regions are generally characterized by tissue in which sufficient thermal tissue injury occurred to result in cell death without causing thermal fixation. Subsequently, the tissue undergoes the reabsorption and the classical pathway of wound healing with subsequent fibrosis (scar) formation. The LVR described herein is generally accomplished by fibrosis of the lung tissue following vapor treatment.

Thermal fixation is generally characterized by dead tissue that received sufficient hyperthermic exposure to morphologically mimic chemical (formalin) fixation. The exposure is sufficient to completely denature cellular and extracellular matrix proteins in situ so that the natural processes of enzymatic tissue autolysis and breakdown after lethal injury are inhibited. As a result, the tissue resists reabsorption and remodeling via a wound healing pathway and is generally walled off by the body similar to a foreign body.

Other types or degrees of injury that may be desired to induce in lung tissue include pulmonary edema, hyaline membranes, acute or chronic inflammation, post-obstructive change, atelectasis, and bronchial, bronchiole, and alveolar parenchyma with minimal to absent histologic injury.

When vapor is delivered to the target lung tissue, it undergoes a phase change from vapor to liquid. The thermal energy released during this phase change is transferred to the lung tissue. This rapidly heats the tissue and induces such injuries as coagulative necrosis (followed by fibrosis), thermal fixation, tissue collapse, shrinkage, neointima hyperplasia, or any other desired injury to the lung tissue such as those described above. Thermal energy may also be conducted to the tissue from the hot vapor and/or vapor condensate.

Fibrosis following necrosis produces a reduction in volume of the lung (due to the volumetric reduction of non-viable lung tissue). By reducing lung size, the remaining lung and surrounding muscles (intercostals and diaphragm) are able to work more efficiently. This makes breathing easier and helps patients achieve improved quality of life allow for improved breathing mechanics, including increased volume per breath and $O_2$ uptake increase.

The volume of the lung may also be immediately reduced (as opposed to fibrosis which generally causes reduction in volume over a longer period of time) from shrinking and or denaturing of collagen.

The degree of LVR is generally dose dependent; the higher the dose, the more the lung volume is reduced. The degree of LVR may not be determined until weeks or months after treatment. In some embodiments the dose dependency of the LVR may not begin to be apparent until about 2 to about 4 months. This gradual reduction in LVR may help prevent or minimize acute tearing of pre-existing adhesions that can produce pneumothorax in some emphysema patients.

Another advantage to using vapor treatments described herein to reduce the volume to the lung is that this technique is an effective method even in the presence of collateral ventilation.

In addition to the desired degree of injury (which depends on the lung condition to be treated), the amount of lung tissue to be treated will partially determine the treatment parameters. For example, the delivery parameters could be different for treating an entire lobe of the lung as opposed to treating a segment or sub-segment of a lobe. As used herein, lung tissue includes both native lung tissue in addition to any other growth or non-lung tissue that may be present in or on the lung, such as, for example without limitation, a tumor.

One aspect of the invention is a method of determining treatment parameters for applying energy to lung tissue with vapor to bring about a desired injury to the lung tissue (e.g., necrosis/fibrosis, thermal fixation). The method includes identifying a lung condition or disease to be treated (e.g., COPD, a lung tumor), imaging at least one segment or sub-segment of the lung to be treated, determining an amount (e.g., the mass or volume) of the lung tissue of the segment or sub-segment to be treated based on the imaging, determining an amount of energy to be delivered to the segment or sub-segment based on the amount of the lung tissue, and determining a duration for delivering the vapor based on the amount of energy to be delivered and an energy delivery rate of a vapor delivery system which delivers the vapor.

Figure 6:
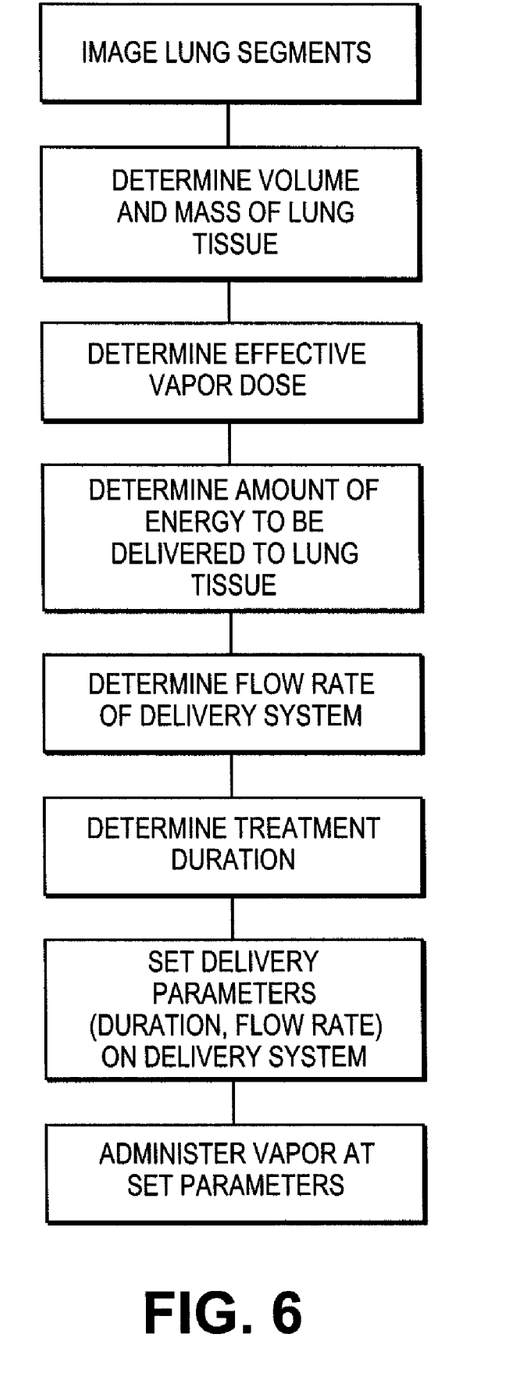
FIG. 6 is a flow chart illustrating an exemplary method for determining vapor delivery parameters to treat lung tissue.

FIG. 6 shows an exemplary method for determining vapor delivery parameters to treat lung tissue. These steps are not necessarily sequential and/or dependent, of course.

Identifying a lung condition or disease, such as COPD or a lung tumor, can be accomplished by known medical tests and procedures.

Imaging a segment or sub-segment of the lung to be treated can be performed by a number of medical imaging techniques, such as, without limitation, CT, MRI, ultrasound, and x-ray.

The total volume of the lung segment or sub-segment, the air volume of the lung segment or sub-segment, and the tissue volume of the lung segment or sub-segment can then be determined using the data from the imaging procedure. The imaging, volume, and density determinations of the lung segment or sub-segment to be treated can be performed and supplied using such software as VIDA Emphysema Profiler 1.1 software (VIDA Diagnostics, Inc. Iowa City, Iowa USA). Further information on lung airway segmentation using CT can be found in Intrathoracic airway trees: segmentation and airway morphology analysis from low-dose CT scans. Tschirren, J.; Hoffman, E. A.; McLennan, G.; Sonka, M., Medical Imaging, IEEE Transactions on, Volume 24, Issue 12, December 2005 Page(s): 1529-1539.

Depending on the desired degree of injury for the lung tissue, a safe and efficacious amount of energy, or dose of energy (e.g., calories/gram), to be applied to the lung tissue must be determined to accomplish that result. In general, as the dose increases the degree of injury to the tissue increases. Doses of vapor from about 5 cal/g to about 40 cal/g will generally result in coagulative necrosis with little, or even no, thermal fixation. The degree of thermal fixation will generally increase as the dose increases above 40 cal/g. The desired degree of injury to the lung tissue can therefore be controlled by altering the dose of vapor applied to the tissue.

To cause necrosis, the energy dose in preferred embodiments varies from about 5 cal/g to about 40 cal/g. These limits are, however, not intended to be definitive limitations of the doses applied, as other delivery parameters described below (e.g., delivery rate, delivery duration, etc.) may allow different doses to be applied to accomplish the same or similar injury to the tissue.

After determining the dose to apply to the tissue, the amount of total energy that needs to be applied by a delivery system (such as the delivery system described below) to the tissue is determined. This is done generally by multiplying the dose (cal/g) by the amount of tissue to be treated (grams) to determine the amount of energy (cals) to deliver.

The delivery (or flow) rate, or the rate at which the delivery system delivers the energy, generally determines the duration that the vapor will be delivered to deliver the determined amount of energy. For example, to deliver 300 calories to a segment of the lung at a delivery rate of 30 cals/second, the treatment duration would be 10 seconds. The delivery rate is generally between about 20 cals/second to about 200 cals/second. Again, these limitations are not intended to be definitive limitations and the delivery rate may be higher or lower depending on other treatment and/or delivery parameters.

Treatment times can vary depending on the volume, mass to be treated, and the desired injury to the tissue. Treatment times can vary from about 2 seconds to about 30 seconds. In some embodiments for causing necrosis to reduce the volume of the lung, the safe and effective treatment time is between about 4 and about 10 seconds. To thermally fix the lung, for example, the treatment time may be longer in order to injure the tissue to a greater degree.

The delivery rate can be set via controls of a delivery system, such as the system described below. Once the user sets the delivery rate, the generator will establish the requisite amount of pressure in the generator to deliver the vapor at the desired rate by adjusting the amount of heat applied in the generator. Changing the delivery rate setting will cause the generator to adjust the amount of pressure in the generator. The pressure in the vapor generator can range from between about 10 psi (69 kPa) to over about 100 psi (689 kPa).

Table 1 shows an example of software-determined volume data from imaged lung segments.

TABLE 1

| Lung Segment | Total Volume (cm$^3$) | Tissue Volume (cm$^3$) | Air Volume (cm$^3$) |
|---|---|---|---|
| RB1 | 722.58 | 71.62 | 651.32 |
| RB2 | 361.01 | 49.36 | 312.45 |
| RB3 | 238.31 | 39.39 | 198.92 |

Table 2 shows an example of determining treatment and delivery parameters for causing necrosis based on the volume data for an RB2 lung segment.

TABLE 2

| | |
|---|---|
| Tissue volume | 49.36 cm$^3$ |
| Mass of lung tissue to be treated | 49.36 cm$^3$ × 1 g/cm$^3$ (tissue density) = 49.36 g |
| Energy delivery rate (predetermined) | 39 cal/sec |
| Energy dose to RB2 segment (predetermined) | 5 cal/g |
| Energy to be delivered | 5 cal/g × 49.36 g = 246.8 cals |
| Treatment Time | 246.8 cal/(39 cal/sec) = 6.33 sec |
| Treatment Flow (predetermined and based on selected delivery rate) | Level 6 (19 psi) |

As can be seen from Table 2, the flow level is set by the user to correspond to the desired delivery rate (i.e., in the example, the user will set the flow to level 6 which sets the delivery rate of the system to 39 cal/sec). The generator will then generate the necessary pressure within the generator.

FIGS. 1-5 show an exemplary system and system components for generating and delivering vapor to lung tissue to be treated. The system 10 generally comprises a vapor generator 12, hand-piece 14, and delivery catheter 16.

Figure 1:
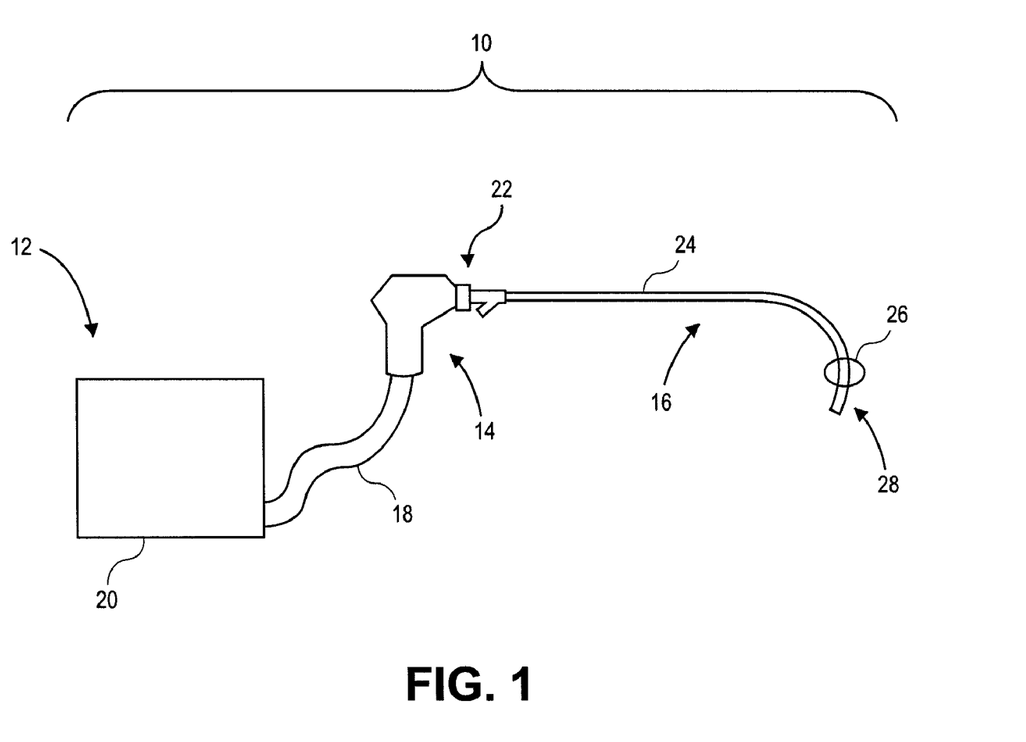
FIG. 1 shows a system for generating and delivering therapeutic vapor to a lung.
Figure 2:
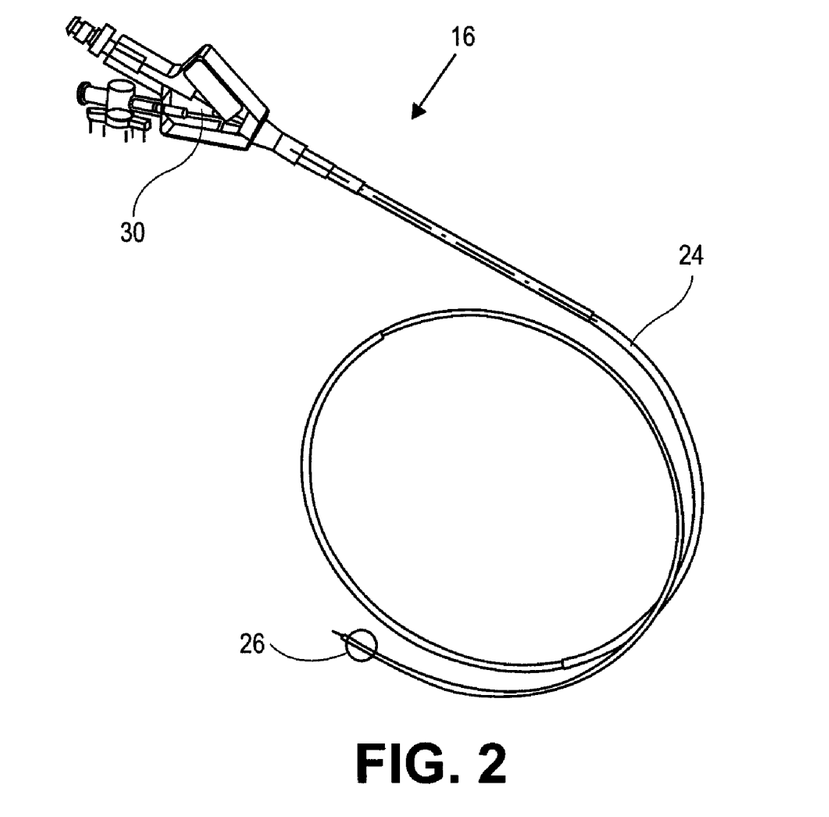
FIG. 2 shows details of a vapor delivery catheter component of the system of FIG. 1.
Figure 3:
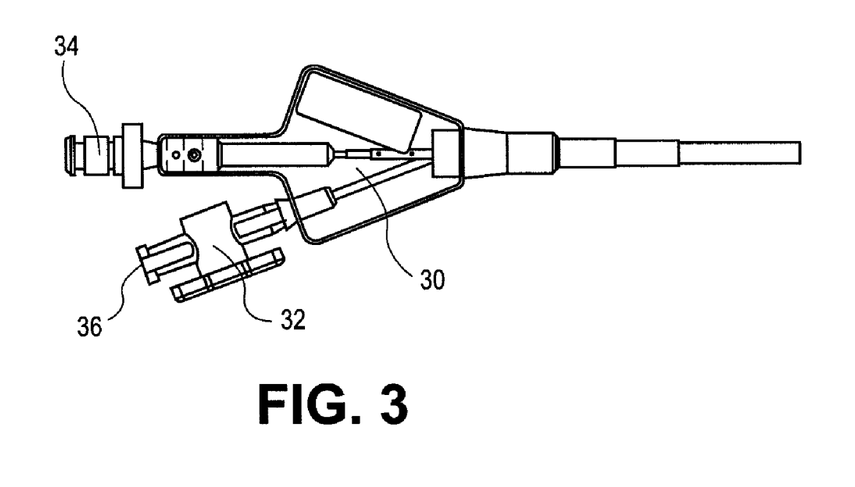
FIG. 3 shows details of the vapor delivery catheter of FIG. 2.

The vapor generator 12 is attached to the hand-piece 14 by tube 18. The generator comprises a pressure vessel 20 containing liquid water (or other biocompatible liquid, such as saline) and steam (not shown), a heating element (not shown) to heat the water, sensors (not shown), and valves (not shown). Hand piece 14 is coupled to the proximal end 22 of catheter.

The catheter is generally used to deliver the heated water vapor (steam) via a bronchoscope (not shown) to a targeted segment or sub-segment of the subject's lung. The catheter 16 generally is comprised of flexible shaft 24 and occlusion balloon 26 located at or slightly proximal to the distal end 28 of the catheter.

Figure 4:
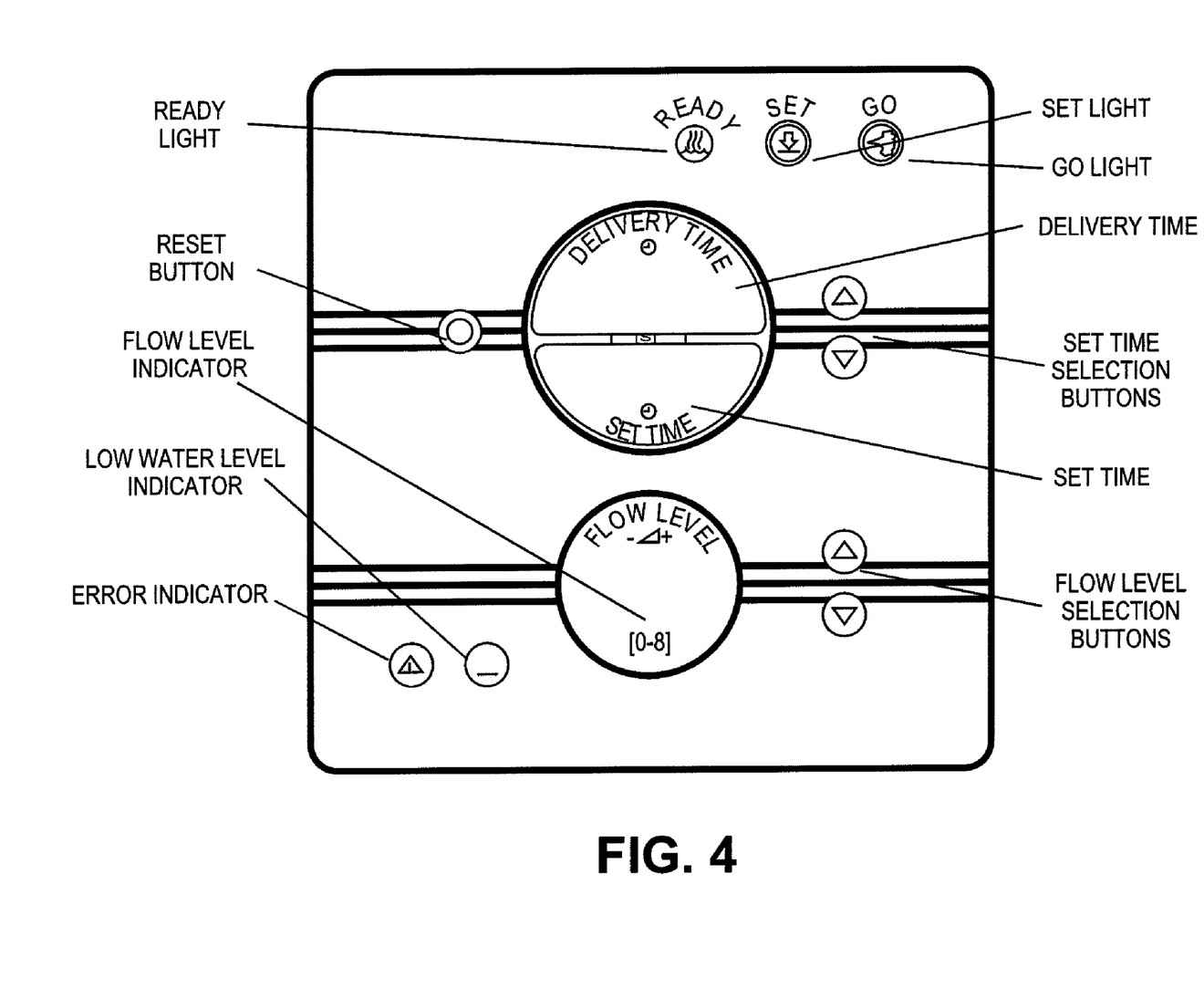
FIG. 4 shows a user interface for use with the system of FIG. 1.

The vapor generator is an electronically controlled pressure vessel that generates and delivers precise amounts of steam via the catheter. The operator selects the flow level and the duration of the vapor treatment (the determination of which is described below) using a user interface on the front panel. An exemplary user interface is shown in FIG. 4. The combination of flow level and delivery time delivers a specific amount of vapor therapy to the patient. While delivery of vapor to the patient is preferably manually triggered by the operator using the handpiece, an electronic controller inside the generator continuously monitors temperatures, pressures, water level, and ensures safety of the software.

The vapor is generally heated to between about 100° C. to about 175° C.

The catheter is preferably non-reusable and supplied sterile. It is comprised of components for occluding the target airway and delivering a dose of vapor from the vapor generator to the targeted lung segment or sub-segment. Manifold 30 (see FIGS. 2 and 3), which is located at the proximal end of the catheter, contains stopcock 32 for attachment of a standard syringe (not shown) to luer connector 36 to inflate the compliant balloon, as well as quick-connect 34 for coupling the catheter to the hand-piece. The catheter shaft is adapted to allow delivery of the catheter through a bronchoscope, and the catheter comprises a balloon near the distal end of the catheter shaft to allow proper sealing of the targeted bronchi.

A general method of delivering vapor to the lung includes advancing the catheter into the region of the lung targeted for treatment, such as a segment or sub-segment of the lung. The balloon at or near the distal end of the catheter tip is inflated to seal the airway. The vapor is then delivered from the distal end of the catheter. The balloon in then deflated and the catheter is withdrawn.

Figure 5:
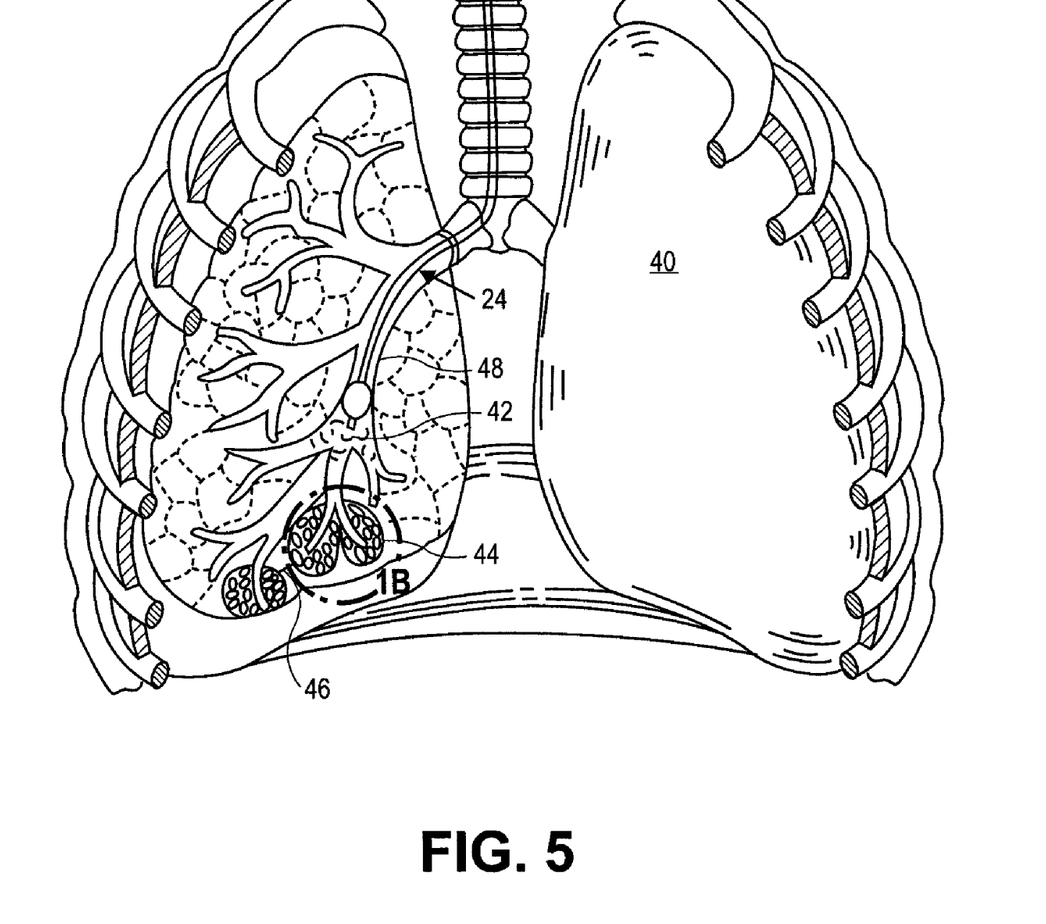
FIG. 5 shows the system of FIG. 1 in use to treat a patient's lung.

FIG. 5 illustrates an exemplary method of treating a patient's lung 40 embodying features of the invention that includes delivering a condensable vapor 42 to tissue defining an air sac or alveoli 44 within a patient's lung 40, so as to injure the tissue of the air sac or alveoli 44, the tissue of terminal bronchioles and tissue of collateral passageways 46.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of applying energy to tissue of a patient's lung to reduce the volume of the lung, the method comprising:
   identifying at least one region of lung including the lung tissue to be treated;
   inserting a delivery device into the lung region;
   delivering vapor through the delivery device to the lung tissue to be treated at a dose between about 5 calories/gram to about 40 calories/gram, wherein the vapor undergoes a phase change to liquid, and energy released during the phase change is transferred to the lung tissue to injure the tissue.

2. The method of claim 1 wherein the region is a lung segment or sub-segment.

3. The method of claim 1 further comprising heating the vapor to at least 100° C. before delivering the vapor.

4. The method of claim 1 wherein the dose delivered causes the lung volume to be reduced over a period of about 4 to about 8 weeks.

5. The method of claim 1 wherein the dose delivered causes the lung volume to be immediately reduced from shrinking and or denaturing of collagen.

6. The method of claim 1 wherein the energy transferred to the tissue causes coagulative necrosis of the lung tissue.

7. The method of claim 6 wherein the coagulative necrosis is followed by fibrosis to effectively reduce the volume of the lung region.

8. The method of claim 6 wherein the energy transferred to the tissue causes substantially no thermal fixation.

9. The method of claim 1 wherein delivering the vapor comprises delivering the vapor at a flow rate of between about 20 calories/second to about 200 calories/second.

10. The method of claim 1 wherein delivering the vapor comprises delivering the vapor for a duration of between about 2 seconds to about 30 seconds.

11. The method of claim 10 wherein delivering the vapor comprises delivering the vapor for a duration between about 4 and about 10 seconds.

12. The method of claim 1 further comprising generating the vapor in a generator disposed outside of the patient.

13. The method of claim 1 wherein delivering comprises exposing the lung tissue to the vapor.

14. The method of claim 1 wherein the dose is between about 5 cal/g and about 20 cal/g.

15. The method of claim 1 wherein the dose is between about 5 cal/g and about 10 cal/g.

16. The method of claim 1 wherein the dose is between about 20 cal/g and about 40 cal/g.

17. The method of claim 1 wherein the delivering step comprises ablating microvasculature in the lung tissue.

* * * * *